(12) United States Patent
Gho

(10) Patent No.: US 6,399,057 B1
(45) Date of Patent: Jun. 4, 2002

(54) METHOD FOR THE PROPAGATION OF HAIR

(75) Inventor: Conradus Chosal Gho, Bunde (NL)

(73) Assignee: Gho'st Holding B. V., Bunde (NL)

( * ) Notice: Subject to any disclaimer, the term of this patent is extended or adjusted under 35 U.S.C. 154(b) by 0 days.

(21) Appl. No.: 09/380,580

(22) PCT Filed: Mar. 5, 1998

(86) PCT No.: PCT/NL98/00129

§ 371 (c)(1),
(2), (4) Date: Oct. 20, 1999

(87) PCT Pub. No.: WO98/47471

PCT Pub. Date: Oct. 29, 1998

(30) Foreign Application Priority Data

Mar. 5, 1997 (NL) .............................. 1005445

(51) Int. Cl.⁷ ...................... A01N 63/00; A01N 65/00; A61K 7/06
(52) U.S. Cl. ...................... 424/93.7; 424/70.1
(58) Field of Search .............................. 424/93.7, 70.1; 623/15; 436/63

(56) References Cited

U.S. PATENT DOCUMENTS 5,556,783 A * 9/1996 Lavker et al.
5,635,387 A * 6/1997 Fei et al.
6,050,990 A * 4/2000 Tankovich et al.

FOREIGN PATENT DOCUMENTS

| EP | 0236014 | * | 2/1987 |
| EP | 236 014 |   | 9/1987 |
| EP | 682 107 |   | 11/1995 |
| WO | WO 92/00376 | * | 1/1992 |
| WO | WO 92/07877 |   | 5/1992 |
| WO | WO 95/01423 |   | 1/1995 |
| WO | WO 96/32961 |   | 10/1996 |

OTHER PUBLICATIONS

Lenoir et al., Developmental Biology, 130: 610–620. Outer root sheath cells of human hair follicle are able to regenerate a fully differentiated epidermis in vitro, 1998.*

Schirren et al. The AM J of Dermatopathology, 19(4): 334–340. Fetal and adult hair follicle: An immunohistochemical study of anticytokeratin antibodies in formalin-fixed and paraffin–embedded tissue, Apr. 1997.*

* cited by examiner

Primary Examiner—Christopher R. Tate
Assistant Examiner—Michele C. Flood
(74) Attorney, Agent, or Firm—Sughrue Mion, PLLC

(57) ABSTRACT

Method of reproduction of hair, which method comprises the following steps:

(1) removal of hair in the anagen phase from one or more donor regions in such a way that the bulb characteristic of hair in the anagen phase is still attached to the hair removed, (2) culture of hair follicle cells from the hair removed, under conditions such that the hair follicle cells are able to multiply, and (3) implantation of the cultured hair follicle cells in the receptor regions.

Medium which comprises at least one suitable serum-free keratinocyte culture medium and extracts of at least one human mast cell line and method for culturing hair follicle cells from hairs in the anagen phase, wherein one or more hairs in the anagen phase are placed in said medium.

11 Claims, No Drawings

METHOD FOR THE PROPAGATION OF HAIR

The present invention firstly relates to a method for the reproduction of hair. The invention also relates to a method for culturing hair follicle cells from anagenetic hairs in the anagen phase, to a medium that is highly suitable for culturing hair follicle cells, to a method for the preparation of such a medium and to a precursor medium.

A method for the reproduction of hair is disclosed in European Patent Application 0 236 014 in which epidermal follicle cells of the desired hair type are removed from the scalp skin of a patient. The epidermal follicle cells are then cultured in a culture medium which preferably contains growth factors. In a subsequent step, an opening is made in the epidermis of the patient's scalp and, via said opening, the cultured epidermal follicle cells are introduced into the dermis next to the epidermis. The disadvantage of this method is that it comprises an invasive method and that the cells are not placed directionally, as a result of which many cells are necessary and the probability of regeneration of hair is much lower. In this method, use is also not made of autologous (cultured) $CD34^+$ cells.

The essential growth structures of hair are the so-called hair follicles, which are present in the skin. The hair follicle cells or keratinocytes reproduce from these hair follicles and during their path to the skin surface the cytoplasm of said cells is converted by a large number of complex processes into the tough and resilient material which is known as hair. The growth cycle of hair can be subdivided into three phases: the anagen phase or growth phase, the catagen phase or transitory phase and the telogen phase or dying phase. The hair follicle is unique because of the cyclic nature of hair formation and hair growth. Specifically, the hair follicle is the only part of the body to have a growth nucleus, from which new hairs can be produced after removal of the old hair.

It is known that hair follicle cells from plucked human hair can be cultured. It is also known that it is possible using such cultured cells to form a differentiated epidermis or a fully developed epidermis, both in vitro and in vivo. Cultured hair follicle cells from mice can stimulate hair growth when said cells are implanted into test animals. However, to date it has not proved possible to achieve new hair growth in humans in those locations where there is undesirably no (longer any) hair with the aid of cultured autologous hair follicle cells.

People usually find baldness to be undesirable from the cosmetic and aesthetic standpoint. However, baldness frequently occurs and it is a known phenomenon that in particular men also become balder as they got older. This form of baldness is known as alopecia androgenetica. To date it is not precisely known why certain parts of the scalp are susceptible to this alopecia androgenetica and other parts are not. However, with women as well it regularly occurs that the hair becomes thinner and even threatens to largely disappear. For women in particular this is highly undesirable from the cosmetic and aesthetic standpoint.

A known technique for combatting baldness is to transplant hair. With this procedure hair from a donor region covered in hair, which frequently is located on the back of the head, is removed, including the skin, and cut into small pieces, which usually then have only one to three hairs. These pieces are then implanted in the bald region (receptor region). A major disadvantage of this method is that it is at the cost or the donor region. Specifically, hair is removed from this region and this hair does not return again. The transplantation technique therefore offers limited possibilities.

The aim of the present invention is to provide a technique with the aid of which bald patches can be provided with hair again, but which does not have the disadvantages of hair transplantation which have been outlined above. A further aim or the invention is to provide a method with which new hair growth on bald patches can be achieved in humans with the aid of cultured hair follicle cells. A further aim of the invention is to provide a method which is relatively simple to carry out.

Said aims are achieved with the method according to the invention, wherein hair is, as it were, reproduced. Specifically, according to the invention the hair is removed from a donor region in such a way that new hairs come back in its place whilst new hair follicle cells are cultured from the hairs removed, from which cells, in turn, new hair can form.

The invention therefore relates to a method for the reproduction of hair, which method comprises the following steps:

(1) removal of hair in the anagen phase from one or more donor regions in such a way that the bulb characteristic of hair in the anagen phase is still attached to the hair removed.

(2) culture of hair follicle cells from the hair removed, under circumstances such that the hair follicle cells are able to multiply, and (3) implantation of the cultured hair follicle cells in the receptor regions, wherein:

the hair in the anagen phase is removed by plucking hair out of the donor region or the donor regions, followed by selection of suitable hairs in the anagen phase, the hair follicle cells are cultured in a culture medium which is optionally supplemented with (a) at least one human mast cell line and/or autologous (cultured) $CD34^+$ cells, or (b) one or more extracts of the human mast cell line(s) and/or of the $CD34^+$ cells and/or (c) growth-stimulating agents, and the cultured follicular hair cells and/or the autologous (cultured) $CD34^+$ cells are implanted in the pores of the receptor region.

According to the invention, only one hair follicle cell or one autologous (cultured) $CD34^+$ cell or a combination of these two cells can be introduced although a plurality of cells is usually mentioned in the description.

The method according to the invention has the major advantage that hair growth can be achieved again on bald patches without this being at the expense of the donor region.

Step (1) of the method according to the invention comprises the removal of hair in the anagen phase from a donor region where such hairs are located. As explained above, hair growth comprises three phases: an anagenous, a catagenous and a telogenous phase. Only hairs which are in the anagenous phase are suitable for the method according to the invention. Compared with hairs in the catagen and telogen phases, such hairs in the anagen phase are characterized in that they have a—frequently pigmented—bulb of a shape characteristic for hairs in the anagen phase at the bottom of the hair. This is generally known and to an experienced eye a hair in the anagen phase is therefore also immediately recognizable from the shape of the bulb. In the case of doubt the use of a microscope can provide a definite answer. The removal of hairs in the anagen phase can therefore be effected in various ways, as long as the bulb characteristic of hairs in the anagen phase is still attached to the hair removed.

The number of hairs in the anagen phase needed to culture a suitable quantity of hair follicle cells is hardly subject to specific limits since in principle an unlimited number of hair follicle cells can be cultured from a single hair. Specifically, subcultures can, in turn, be cultured from the first culture and, in turn, several cultures can be cultured from every subculture. In practice, 3 to 10 hairs in the anagen phase will be ample. The hairs which ultitmately are formed in the receptor region from the cultured hair follicle cells assume the characteristics of the hairs from the donor region from which the hair follicle cells were cultured. Therefore, a region which is not susceptible to alopecia androgenetica is taken as a suitable donor region. However, this is not essential.

Since the difference between hairs in the various growth stages can be seen most clearly once the hairs have been removed, the hairs from the donor region are removed by plucking hair out of the donor region and selecting the suitable hairs in the anagen phase. Tweezers are, for example, very suitable for plucking hair from the donor region.

In step (2) of the method according to the invention the hairs are cultured from the hair removed, under conditions such that the hair follicle cells are able to multiply. In principle, the hair follicle cells can be cultured from the hairs by the known method. Culture media for this purpose are available commercially and any associated growth supplements are freely available. Such culture media are also termed serum-free keratinocyte culture media and usually contain essential and non-essential amino acids, vitamins, trace elements, organic constituents and inorganic salts. Such culture media can also be combined with growth supplements, which contain growth factors, hormones, antibiotics and tissue extracts, such as, for example, BPE (Bovine Pituitary Extract), insulin, hydrocortisone, HEGF (Human Epidermal Growth Factor), TGF (Transformal Growth Factor), L-cysteine, L-leucine and gentamicin. According to the invention, particularly good results are obtained if, in step (2) of the method according to the invention, use is made of a culture medium which, in addition to the known culture media described above, is optionally supplemented with one or more growth supplements, and/or is supplemented with one human mast cell line and/or autologous (cultured) CD34$^+$ cells (CD34$^+$ positive cells) or one or more extracts of the human mast cell line(s) and/or of the CD34$^+$ cells and/or growth-stimulating agents. Preferably, only cultured CD34$^+$ cells are used because these cells are native to the body. Human mast cells are known per se They contain various growth factors and are produced and consumed in various different sites in the body. The extracts of the human mast cell line and/or autologous (cultured) CD34$^+$ cells and/or growth-stimulating agents contain growth factors. However, to date such extracts of the human mast cell line and/or autologous (cultured) CD34$^+$ cells and/or growth-stimulating agents have not been used in media for culturing hair follicle cells. A human mast cell line from which the extracts can be used, is HMC-1 (Human Mast Cell line 1) or a cell line derived therefrom, such as the subclones 5C6 and KU812. Mast cell lines such as HMC-1 and subclones thereof are commercially available. According to the invention, instead of mast cells, autologous (cultured) CD34$^+$ cells or a combination of two or more of these cell types can be used.

The extracts of the human mast cell line and/or autologous (cultured) CD34$^+$ cells and/or growth-stimulating agents can very suitably be introduced into the medium by adding at least one degranulating agent to the serum-free keratinocyte culture medium containing the human mast cell line, a subclone thereof and/or autologous (cultured) CD34$^+$ cells and/or growth agents. An inorganic salt can also be added to optimise the action of the degranulating agent. A suitable salt in this connection is $CaCl_2$. The degranulating agent then, as it were, cuts the mast cells and/or the autologous (cultured) CD34$^+$ cells into smaller pieces (degranulation) as a result of which the growth factors are released into the medium. After degranulation, the residues of the mast cells and/or the autologous (cultured) CD34$^+$ cells can be removed, for example by means of centrifuging. The resultant, conditioned medium can then be used to culture the hair follicle cells.

Degranulating agents are known per se and can roughly be divided into three groups:
hormones, such as oestrogens and bradykinin,
neurotransmitters and antigens, such as apitoxin. Substance P and Ig E, and
synthetic agents, such as Compound 48/80 and Ionophore A23187. Those degranulating agents which are capable of degranulating the mast cells optionally used are suitable for use in the method according to the invention.

An alternative is first separately to prepare the extracts or the human mast cell line and/or autologous (cultured) CD34$^+$ cells and/or growth agents and to add these extracts as such to the serum-free keratinocyte culture medium.

The conditions under which the hair follicle cells are cultured in step (2) can vary substantially and are dependent on, inter alia, the medium used. However, it has been found that the culturing of the hair follicle cells at a temperature of 30–40° C., preferably in an incubator so that the temperature can be kept constant, in an atmosphere which is saturated with water and which contains 3–10% by volume $CO_2$ in addition to the other customary constituents of air in the customary quantities gives good results. However, these conditions are in no way restrictive and other conditions can therefore also be used. The culture period varies per culture, usually from 1 hour to 40 days. In order to obtain a good result, it is preferable to replace the medium by fresh medium every 2 to 5 days.

Step (2) of the method according to the invention can be carried out in a single culture step, but can also be carried out in several sub-steps by culturing subcultures from the initial culture or cultures. This can be carried out by taking a sufficiently large number of hair follicle cells from the main culture when the latter contains sufficient hair follicle cells. The hair follicle cells from the main culture are cultured in turn, preferably —but not necessarily— in the same culture medium as that in which the original main culture was cultured. In the course of time it is possible, if desired, to culture yet further cultures from said subcultures, etc. etc.

After the hair follicle cells have been cultured they must be detached from the substrate on which they have been grown. This can be carried out by the known methods, for example by making use of a trypsin solution (0.1–0.5% by weight in water), optionally in combination with an EDTA solution (0.01–0.05% by weight) in PBS (Phosphate Buffered Saline). Such methods are known per se. Before the cultured hair follicle cells are used in step (3), the most cells and/or autologous (cultured) CD34$^+$ cells can, if desired, be removed.

In step (3) or the method according to the invention, the cultured hair follicle cells and/or autologous (cultured) CD34$^+$ cells are implanted in the skin in the receptor region. It has been found that very good results are obtained when the cultured hair follicle cells and/or autologous (cultured)

CD34+ cells are implanted directly into the pores of the receptor region. If the pores are difficult to see, which can with a pale skin colour in particular, the pores can be made more readily visible by applying a (usualy yellow-coloured) liquid to the skin in the receptor region, which becomes darker in colour in the positions where the pores are located as a result of the secretion of the perspiration from the sweat glands present in the pores. An example or such a liquid is a 1–10% solution of o-phthaldialdehyde in, for example xylene or ethyl ether, as described by L. Juhlin and W. B. Suelley in Nature, Jan. 28, 1967, page 408.

Preferably a quantity of a suspension of cultured hair follicle cells and/or autologous (cultured) CD34+ cells is introduced into each pore such that said quantity contains sufficient hair follicle cells and/or autologous (cultured) CD34+ cells to allow a hair follicle to develop from which a hair is able to grow. The number of cultured hair follicle cells and/or autologous (cultured) CD34+, cells needed to cause a hair follicle to form is highly dependent on the degree of differentiation or the growth potential of the cultured cells. Naturally, fewer cultured cells will be needed when the cultured hair follicle cells and/or autologous (cultured) CD34+ cells have a relatively high degree of differentiation than when the cultured cells have a relatively low degree of differentiation. There are a large number of factors which influence the degree of differentiation of the cultured hair follicle cells and/or autologous (cultured) CD34+ cells. For example, the medium used and the culture time are factors which play a role. Preferably, a suspension of the cultured hair follicle cells and/or autologous (cultured) CD34+ cells in the medium in which said cells were cultured is used. The suspension preferably has a hair follicle cell concentration which is such that 0.015–5 $\mu$l, preferably 0.1 to 0.5 $\mu$l, of suspension per pore can suffice. A small quantity such as this is preferably injected into the pore with the aid of a metering device which is provided with a hollow needle. preferably an 18 to 40 Gauche (G) needle. The metering device used can be, for example, an electronic metering system for a pipette, a 18–40 G needle being fitted on the end of the metering hose or of the pipette. In the light of the average size of the pores in, in particular, the scalp, it is preferable to use a hollow 34 G needle. However, smaller or larger needles can also be used on other parts of the body. It is also possible and preferable for the suspension to be injected with an (electronic) repeating injection-metering apparatus such as an insulin pen. In that case, a needle specially developed for the purpose, that is to say a "follicle-conducting needle", is also used to introduce the cells at the desired position and to damage the skin as little as possible. A follicle-conducting needle is a needle which is flexible and minuscule and also which the hair follicle can follow.

During the injection of the suspension, substances can also be introduced at the same time which keep the cells alive for longer. Examples of such substances are Minoxidil and other growth-stimulating agents.

The invention also relates to a method for culturing hair follicle cells from hairs in the anagen phase, one or more hairs in the anagen phase being placed in a medium which is supplemented with one suitable serum-free keratinocyte culture medium and, optionally, supplemented with one human mast cell line and/or autologous (cultured) CD34+ cells or one or more extracts of the human mast cell line(s) and/or of the CD34+ cells and/or growth-stimulating agents. The way in which such a medium can be obtained has already been described above.

As far as the preferences with regard to the various constituents of the medium to be used and to the culturing conditions are concerned, these are the same as those for the medium and the conditions employed in step (2) of the method already described above. Therefore, it is preferable to use one mast cell line, a subclone thereof and/or autologous (cultured) CD34+ cells and/or growth-stimulating agents. Suitable conditions comprise a culture temperature of 30–40° C. in an atmosphere which is saturated with water and contains 3–10% by volume of $CO_2$.

The invention also relates to a medium for culturing hair follicle cells from hairs it the anagen phase and to a method for the preparation of said medium. The medium according to the invention comprises at least one suitable serum-free keratinocyte culture medium, optionally supplemented with one human mast cell line and/or autologous (cultured) CD34+ cells or extracts of the human mast cell line(s) and/or of the CD34+ cells and/or growth-stimulating agents. The special feature of such a medium is, in particular, that it contains growth factors originating from one or more human mast cell lines and/or autologous (cultured) CD34+ cells.

A preferred medium comprises a serum-free keratinocyte culture medium and extracts of the human most cell line HMC-1 or a cell line derived therefrom, such as 5C6 or KU812 or autologous (cultured) CD34+ cells. Further details on the constituents of the medium according to the invention have already been given above.

The method for the preparation of said medium comprises the following steps:

(a) addition of at least one mast cell line, subclone thereof and/or autologous (cultured) CD34+ cells and/or growth-stimulating agents and optionally one degranulating agent, optionally in combination with an organic salt, such as, for example, $CaCl_2$, to a serum-free keratinocyte culture medium;

(b) degranulation of the mast cell line(s), subclones thereof and/or autologous (cultured) CD34+ cells, so that the growth factors are released into the medium; and (c) optionally removal of the mast cells and/or autologous (cultured) CD34+ cells from the medium, for example by centrifuging, after which the (conditioned) medium is obtained.

According to the invention, the mast cells and/or the CD34+ cells and/or the residues thereof are removed from the medium.

The conditions under which this method can be carried out are not particularly critical and will be obvious to any person skilled in the art. The degranulating agent used in step (a) is preferably Compound 48/80 in combination with $CaCl_2$.

Finally, the invention relates to a precursor medium for culturing hair follicle cells from hairs in the anagen phase which medium comprises at least one suitable serum-free keratinocyte culture medium and which is optionally supplemented with one human mast cell line and/or autologous (cultured) CD34+ cells or one or more extracts of the human mast cell line(s) and/or or the CD34+ cells and/or growth-stimulating agents and/or at least one degranulating agent. Said precursor medium can be used as such for preparing therefrom a suitably conditioned medium for culturing hair follicle cells from hairs in the anagen phase. This can be performed simply by carrying out the degranulation if both a human mast cell line and/or autologous (cultured) CD34+ cells is/are present as well as degranulating agent. If one of the two is absent, that is to say the mast cells and/or the CD34+ cells and the degranulating agent, respectively, the missing component must be first added before degranulation of the mast cells can be carried out.

What is claimed is:

1. A method for the cosmetic reproduction of hair, which method comprises:
   (a) removing hair in the anagen phase from one or more donor regions by plucking so that a bulb is still attached to the hair removed, wherein the removing of hair in the anagen phase is done by plucking the hair out of the donor region(s), and selecting hairs in the anagen phase;
   (b) culturing keratinocytes from the hair removed under conditions whereby keratinocytes multiply, wherein the keratinocytes are cultured in a culture medium supplemented with (i) at least one human mast cell line and/or autologous cultured $CD34^+$ cells, or (ii) one or more extracts of a human mast cell line(s) and/or of the autologous $CD34^+$ cells, and/or (iii) growth-stimulating agents; and
   (c) introducing the cultured keratinocytes into the pores of receptor regions.

2. Method according to claim 1, wherein the keratinocytes are cultured in a culture medium supplemented with one human mast cell line, a subclone thereof and/or autologous cultured $CD34^+$ cells, and/or growth-stimulating agents.

3. Method according to claim 2, wherein the human mast cell line is one human mast cell line and/or an autologous cultured $CD34^+$ cell line.

4. Method according to one of the preceding claims, wherein the keratinocytes are cultured at a temperature of 30–40° C. in an atmosphere which is saturated with water and contains 3–10% by volume of $CO_2$.

5. Method according to claim 1, wherein a quantity of a suspension of cultured keratinocytes and/or autologous cultured $CD34^+$ cells is introduced into each pore whereby said quantity contains sufficient keratinocytes and/or autologous cultured $CD34^+$ cells to allow a hair follicle to develop.

6. Method according to claim 5, wherein the quantity of suspension introduced per pore is 0.01–5 $\mu$l.

7. Method according to claim 6, wherein the quantity is 0.1–0.5 $\mu$l.

8. Method according to one of claims 5–7, wherein the suspension is introduced into each pore via a metering pipette which is provided with a hollow needle.

9. Method according to one of claims 5–7, wherein the suspension is introduced via a repeating injection-metering apparatus.

10. Method according to claim 9, wherein a follicle-conducting needle is used.

11. The method according to claim 8, wherein the hollow needle is an 18 to 40 gauge needle.

* * * * *